US00RE46721E

(19) United States
(12) Reissued Patent
Schliemann

(10) Patent Number: US RE46,721 E
(45) Date of Reissued Patent: Feb. 20, 2018

(54) METHOD AND DEVICE FOR THE METERED DISPENSING OF A MEDIUM

(71) Applicant: Stevanato Germany GmbH, Bad Oeynhausen (DE)

(72) Inventor: Eric Schliemann, Radolfzell (DE)

(73) Assignee: Stevanato Germany GmbH, Bad Oeynhausen (DE)

(21) Appl. No.: 15/261,070

(22) Filed: Sep. 9, 2016

Related U.S. Patent Documents

Reissue of:
(64) Patent No.: 8,826,750
Issued: Sep. 9, 2014
Appl. No.: 12/532,516
PCT Filed: Mar. 25, 2008
PCT No.: PCT/EP2008/002344
§ 371 (c)(1),
(2) Date: Dec. 29, 2009
PCT Pub. No.: WO2008/116311
PCT Pub. Date: Sep. 25, 2008

(30) Foreign Application Priority Data

Mar. 22, 2007 (DE) ..... 10 2007 014 418

(51) Int. Cl.
*B01L 3/02* (2006.01)
*B01L 3/00* (2006.01)
*A61M 5/315* (2006.01)

(52) U.S. Cl.
CPC ..... *B01L 3/0224* (2013.01); *A61M 5/3155* (2013.01); *A61M 5/3156* (2013.01); *A61M 5/31505* (2013.01); *A61M 5/31563* (2013.01); *A61M 5/31591* (2013.01); *B01L 3/50825* (2013.01); *B01L 2200/026* (2013.01)

(58) Field of Classification Search
CPC ..... B01L 3/0224; B01L 2200/026; B01L 3/50825; A61M 5/31591; A61M 5/3156; A61M 5/3155; A61M 5/31563
USPC ..... 73/1.74, 864.01–864.13
See application file for complete search history.

(56) References Cited

U.S. PATENT DOCUMENTS 3,101,751 A 8/1963 Bailin
3,672,369 A 6/1972 Brown
4,048,999 A 9/1977 Kobel
4,084,739 A * 4/1978 Koltz ..... B23K 37/0531 228/168
4,614,267 A 9/1986 Larkin
(Continued)

FOREIGN PATENT DOCUMENTS

DE 2533036 2/1977
EP 0117489 9/1984
EP 0250095 12/1987
(Continued)

OTHER PUBLICATIONS

Partial English Translation of FR 2493515 A1 to Chollet Michel De.*

*Primary Examiner* — Beverly M Flanagan
(74) *Attorney, Agent, or Firm* — Bachman & LaPointe, P.C.

(57) ABSTRACT

A method for metered dispensing of a medium from a container, a dosing pipette ($P_1P_2$) for removing an exactly predetermined amount of the medium to be inserted into the container, wherein the predetermined amount is adjusted on the dosing pipette ($P_1P_2$) prior to removal.

20 Claims, 3 Drawing Sheets

(56) References Cited

U.S. PATENT DOCUMENTS

| | | | | |
|---|---|---|---|---|
| 5,983,733 | A * | 11/1999 | Strandberg et al. | 73/864.11 |
| 2008/0041894 | A1 | 2/2008 | Schliemann | |

FOREIGN PATENT DOCUMENTS

| | | | | |
|---|---|---|---|---|
| FR | 2493515 | | 5/1982 | |
| FR | 2493515 | A1 * | 5/1982 | B01L 3/0224 |
| WO | 0018453 | | 4/2000 | |
| WO | 2004054720 | | 7/2004 | |
| WO | 2005087127 | | 9/2005 | |

* cited by examiner

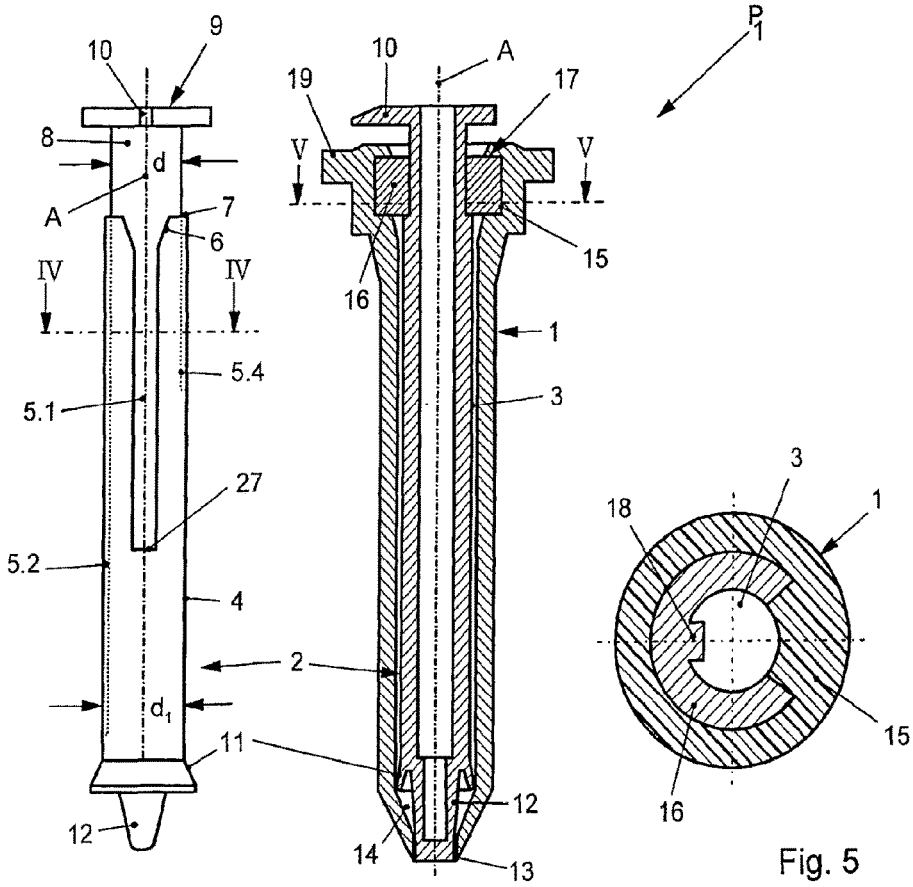
Fig. 3
Fig. 1
Fig. 5
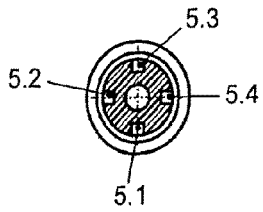
Fig. 4
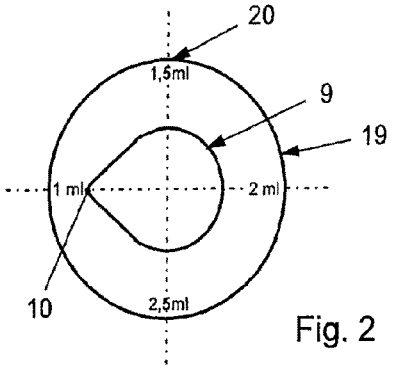
Fig. 2

METHOD AND DEVICE FOR THE METERED DISPENSING OF A MEDIUM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

The invention relates to a method for the metered dispensing of a medium from a container by means of a dosing pipette for removing a precisely predetermined amount of the medium, wherein the predetermined amount is set on the dosing pipette prior to removal.

In many cases in daily life or also in industrial applications, a medium, in particular liquid, has to be removed from a container. This is also particularly true in the field of medicine. Generally speaking, a pipette is known for this, said pipette being inserted into the container and the medium being sucked into a small tube by pressing and releasing a rubber element. In this case, it is not possible to meter the medium to be removed.

WO2004/054720, for example, makes known a metering device for sucking up and dispensing a free-flowing medium from a container, said device having an inlet and an outlet, and inlet and outlet are disposed separated from one another and a metering and displacement chamber is provided between them. Both inlet and outlet are sealable. In this case, however, said metering device is a permanent component of the container itself and cannot be handled separately from said container.

WO 00/18453 also makes known a metering device. However, along with the removal device said device also includes a container and it is only possible to use said devices in combination with one another. A wheel that is situated above the container closure can be rotated to set the desired amount.

It is an object of the present invention to enable a metered removal of a medium from a container and the separate handling of said removal device from the container. In addition, the long-term use of the device is to be improved and faulty dosings avoided.

SUMMARY OF THE INVENTION

The object is achieved in that an opening in the container or a container closure is sealed with a removable sealing plug prior to the insertion of the dosing pipette by the sealing plug being inserted into the container closure from the inside and through the insertion of the dosing pipette being ejected into the interior of the container.

This means that by using a pipette that is insertable into the container, the amount of the medium removed corresponds precisely to the wishes of the user, who can also alter the amount removed, if desired.

If the container is a sealed bag, for example, the dosing pipette directly penetrates said bag. As a rule, however, the container should be a bottle or similar that is provided with a container closure. In this case, it may be advisable to provide the container closure with an opening into which the pipette can be inserted.

Prior to the first insertion of the dosing pipette, said opening should be provided with a sealing plug so that the medium present in the container is not contaminated. By the dosing pipette being inserted, said sealing plug is moved out of its sealing position, remaining, in one exemplary embodiment of the invention, connected to the container closure by means of a securing ring. In this case, the sealing plug can be moved back into the closed position if the container closure is to be used for another bottle.

In another exemplary embodiment of the invention, the sealing plug is inserted into the opening in a detachable manner. It is expelled into the interior of the container by the dosing pipette. If it is of sufficient weight, said sealing plug can then also be used as a mixing element for the medium, if the container has to be shaken before use, for example.

A dosing pipette according to the invention comprises only three elements that are preferably produced from plastics material. The first is a metering housing, into which a plunger, the second, is inserted, which, in its turn, is limited in its stroke movement relative to the metering housing by the third element, namely a cam.

The metering housing is preferably a small elongate, cylindrical tube which, where applicable, tapers downwards and there surrounds an intake opening. Towards the top, said tube is somewhat widened and, in an exemplary embodiment, accommodates a stop ring, from which a cam projects inwards into the clearance of an axial recess of the tube, in which axial recess the plunger is also guided. Said stop ring can be inserted into a corresponding annular recess in the widening and is engaged over towards the top by a flanged edge of the metering housing. Other possibilities for securing the stop ring in the housing are also conceivable here.

In another exemplary embodiment, the cam is a separate element that is inserted into the metering housing into a radial guide. Additional guide rails to facilitate the insertion of the cam can also be provided in said radial recess. In addition, a web is situated in the radial recess, said web being traversed by the cam during insertion and snapping-in behind the cam to prevent the cam sliding out of the recess.

The plunger, in its turn, has a neck region with a smaller diameter than that of a plunger outer surface. Said diameter is selected such that the neck can slide past the cam when the plunger is rotated. Said diameter then continues in grooves which are integrally formed in the plunger outer surface. I.e. the cam can slide in said grooves but at the same time forms an anti-twist protection here such that when the cam engages the grooves, only an axial movement of the plunger relative to the metering housing is possible. So that it is easier for the cam to find the groove associated with it, said groove has a conical groove inlet.

A plurality of grooves is integrally formed in the plunger outer surface distributed about the axis. Said grooves have different lengths so that they also allow for a different stroke of the plunger relative to the metering housing. Said stroke then determines the metering amount that is sucked into a metering space. Said metering space is formed by an end journal of the plunger, an annular lip of the plunger surrounding said end journal and the metering housing and expands during the axial movement of the plunger relative to the metering housing.

The setting of the metering amount is effected by rotating the plunger about the axis as soon as the cam is in the region of the neck of the plunger. To recognize the dose, in this case, markings are provided on a flange of the metering housing, it being possible to determine said markings with an indicator on the plunger. For the user this represents very simple handling, preventing faulty dosing.

The entire structure of the dosing pipette is very sturdy, simple and inexpensive to produce. The entire pipette and the materials used in its production are consumer-friendly in accordance with the guidelines for the pharmaceutical industry and permit clean handling.

BRIEF DESCRIPTION OF THE DRAWINGS

Further advantages, features and details of the invention proceed from the following description of preferred exemplary embodiments and by way of the drawing; in which FIG. 1 shows a longitudinal section through a dosing pipette according to the invention;

FIG. 2 shows a top view of the dosing pipette in FIG. 1;

FIG. 3 shows an outline of a plunger of the dosing pipette in FIG. 1;

FIG. 4 shows a cross section through the plunger in FIG. 3 along the line IV-IV;

FIG. 5 shows an enlarged cross section through the dosing pipette in FIG. 1 along the line V-V;

DETAILED DESCRIPTION

Figure 6:
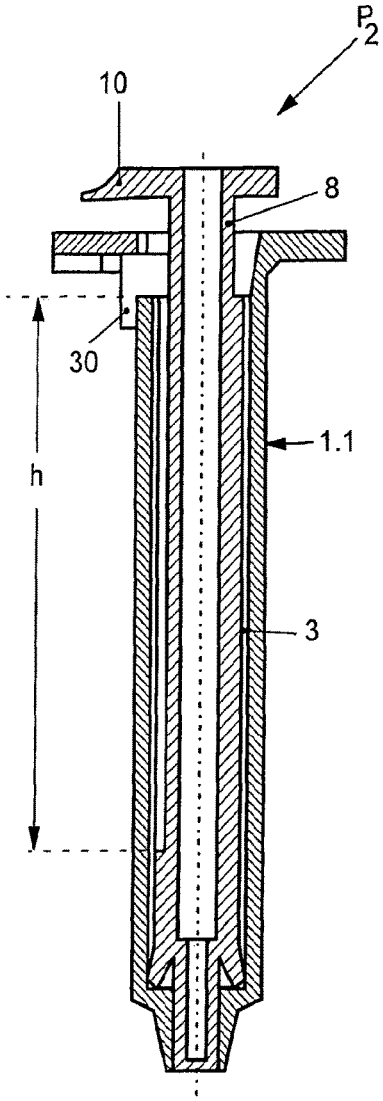
FIG. 6 shows a longitudinal section through another exemplary embodiment of a dosing pipette.

According to FIG. 1, a dosing pipette $P_1$ has a metering housing 1, into which a plunger 2 is inserted. The plunger 2 sits in an axial recess 3 of the metering housing 1 and is rotatable in said axial recess 3 and displaceable along an axis A.

According to FIGS. 3 and 4, the plunger 2 has a plunger outer surface 4, in which a plurality of grooves 5.1 to 5.4 is integrally formed. Each of said grooves 5.1 to 5.4 has a groove inlet 6 that is conical.

The plunger outer surface 4 forms a step 7 towards the top, a neck 8 connecting to said step, a diameter d of the neck 8 being smaller than a diameter $d_1$ of the plunger 2 in the region of the plunger outer surface 4. A disc 9 with a lug 10 (see FIG. 2) is placed onto said neck 8. Said disc 9 can be in the form of a head in an arbitrary manner and can be placed on the neck 8 or integrally formed with said neck.

Towards the bottom an annular lip 11 connects to the plunger outer surface 4, said annular lip widening outwards in a conical manner. In so doing it partially surrounds an end journal 12.

The metering housing 1 tapers towards the bottom and there surrounds an intake opening 13. In the closed position, the plunger 2 sits with its end journal 12 in said intake opening 13. The annular lip 11 abuts sealingly against the axial recess 3 and thus forms, together with the metering housing 1 and the end journal 12, a metering space 14, which expands as the plunger 2 moves along the axis A.

Numerous possibilities are conceivable for the development of the region of the intake opening 13 depending on what the dosing pipette is to be used for. The development for vaginal application can be different to the development for rectal application. If the dosing pipette is conceived as an ointment applicator, spherical geometry can be used so that no injuries are caused. In addition, for example, the end journal 12 can also be provided with an external thread so that it can be screw-connected into a corresponding internal thread of a container. An external thread of this type can also be used, for example, to screw-connect a spherical region which, as mentioned above, avoids injuries. It is also conceivable to attach a sleeve section with an internal thread that then surrounds the end journal 12, the internal thread being capable of being screw-connected to an external thread of a tube. The end journal 12 then engages the tube opening. Many possibilities are conceivable in this case and are to be included in the present invention.

At the oppositely situated end a stop ring 16 is engaged in a housing widening 15 of the metering housing 1 and is retained by a flanged edge 17. A cam 18 projects from said stop ring 16, as shown in FIG. 5, into the clearance of the axial recess 3 of the metering housing 1, said cam, in the position of use, engaging one of the grooves 5.1 to 5.4 of the plunger 2.

Markings 20, which contain information concerning the metering amount, are situated on a housing flange 19. Said metering amount depends on a stroke h that is indicated in FIG. 6.

Figure 9:
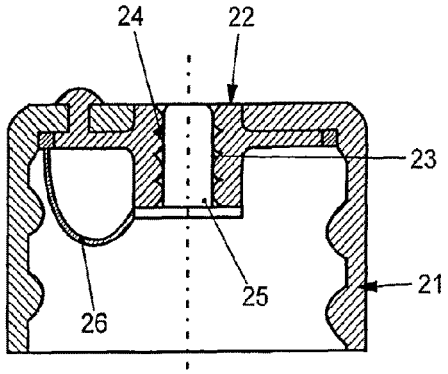
FIG. 9 shows a longitudinal section through a container closure according to the invention.
Figure 10:
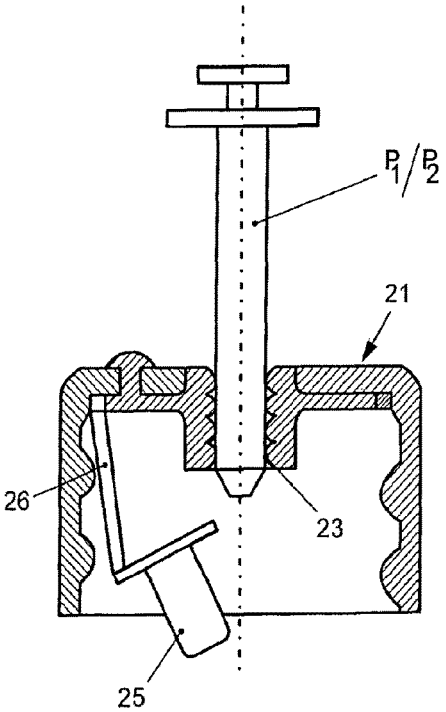
FIG. 10 shows a longitudinal section through the container closure in FIG. 9 with the dosing pipette inserted in the position of use.
Figure 11:
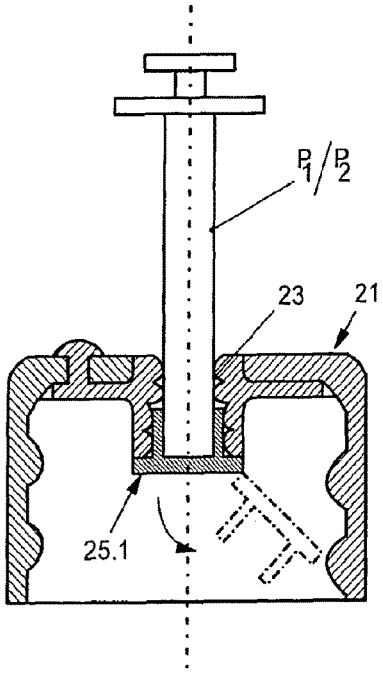
FIG. 11 shows a longitudinal section through another exemplary embodiment of a container closure with the dosing pipette being inserted.

The method of operation of the present invention is also discussed in particular by way of FIGS. 9 to 11:

A container (not shown in any more detail), for example for a medical liquid, is sealed by a container closure 21. This can be a screw-type closure for example. An insert 22, which is preferably produced from a softer plastics material than the container closure 21, is situated in the container closure 21. An opening 23, which is preferably provided with capillaries 24, is integrally formed in said insert 22. A closure plug 25, which is connected to the insert 22 in a captive manner by means of a securing ring 26, sits in the opening 23.

To remove a predetermined amount of medium from the container, the dosing pipette $P_1$, as shown in FIG. 10, penetrates the opening 23, beforehand or afterwards the lug 10 of the plunger 2 having been set to the desired marking determining the metering volume. When the dosing pipette $P_1$ is inserted into the opening 23, the sealing plug 25 is ejected and remains suspended in the interior of the container closure 21, as shown in FIG. 10.

The container together with the container closure and the dosing pipette is then turned upside down and the plunger 2 is moved in the direction of the axis A in the axial recess 3, the medium present in the container thereby being sucked into the metering space 14 in a desired metering volume. During the movement of the plunger 2, the cam 18 moves along the predetermined groove 5.1 to 5.4 until it abuts against the bottom 27 of a groove. This limits its stroke h, which at the same time means that the desired amount of medium is situated in the metering space 14.

The pipette is then pulled out of the opening 23 and, to discharge the medium from the metering space 14, the plunger 2 is moved in the opposite direction along the axis A, the volume of the metering space 14 thereby being reduced. In this case, the annular lip 11 seals off the metering space 14 so that the entire medium can be discharged through the intake opening 13.

Towards the end of this movement, the end journal 12 engages the intake opening 13 and seals the same hermetically relative to the outside so that bacterial contamination in the system is excluded.

If a different metering amount is desired, the plunger 2 is rotated about the axis A and the lug 10 is set to the desired marking 20. This means that the cam 18 then runs down a different groove 5.1 to 5.4 that has a different length and corresponds to the desired metering volume.

FIG. 11 shows that it is also possible for a sealing plug 25.1 to be disposed in a detachable manner in the opening 23. When the dosing pipette $P_1$ pierces the opening 23 in this case, the sealing plug 25.1 falls into the interior of the container, as shown by the dot dash line, and can be used there to mix up the medium when the container is shaken.

Figure 7:
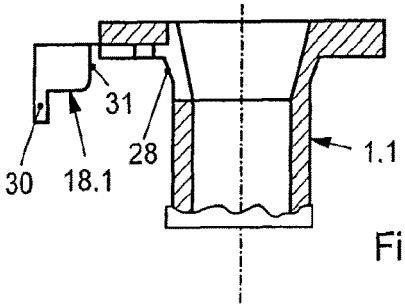
FIG. 7 shows an exploded representation of an enlarged part region of the dosing pipette in FIG. 6.
Figure 8:
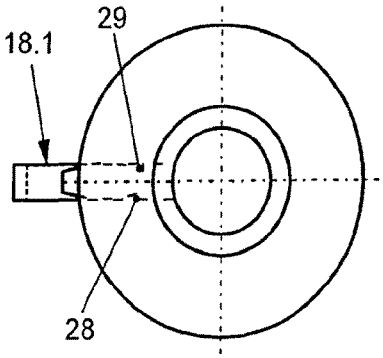
FIG. 8 shows a schematically represented cross section through the dosing pipette in the part region in FIG. 7.

A dosing pipette $P_2$, as shown in FIGS. 6 to 8, differs from the dosing pipette $P_1$ in that the cam is not part of a stop ring, but is a separate element. Said cam 18.1 is inserted laterally in a radial manner into a recess 28 in a metering housing 1.1, it being possible for said inserting to be supported by corresponding guide rails (not shown). In this case, a web 29 is formed in the recess 28 for the cam 18.1, said web, in the end position of the cam 18.1 where said cam, as shown in FIG. 6, abuts against the metering housing 1.1 with a stop 30, engages behind the cam 18.1. In this end position the cam 18.1 sits in the recess such that its end face 31 abuts against the neck of the plunger 3 and can thus slide into the grooves 5.1 to 5.4.

The invention claimed is:

1. A dosing pipette for the metered dispensing of a medium from a container comprising a metering housing, a plunger seated in the housing and axially displaceable therein in a limited manner by rotation of the plunger by a stroke limitation device, the stroke limitation device comprises an interaction between a cam associated with the metering housing and a plurality of grooves of different lengths which are formed axially in an outer surface of the plunger, wherein the cam engages one of the grooves on the outer surface of the plunger thereby (1) determining a volume of the medium to be dispensed and, at the same time, (2) providing anti-twist protection as a result of the interaction between the cam and the associated groove.

2. The dosing pipette as claimed in claim 1, wherein at least one of the plurality of grooves has a groove inlet.

3. The dosing pipette as claimed in claim 1, wherein the cam is part of a stop ring which is inserted into the metering housing.

4. The dosing pipette as claimed in claim 3, wherein the stop ring is flanged into the metering housing.

5. The dosing pipette as claimed in claim 1, wherein the cam is inserted into a recess provided radially in the metering housing and projects into a clearance of an axial recess of the metering housing.

6. The dosing pipette as claimed in claim 5, wherein the cam is clipped into the recess.

7. The dosing pipette as claimed in claim 5, wherein the plunger is supported against the metering housing by an annular lip.

8. The dosing pipette as claimed in claim 5, wherein, in the closed position, the plunger seals an intake opening in the metering housing by an end journal.

9. The dosing pipette as claimed in claim 8, wherein the end journal is conical.

10. The dosing pipette as claimed in claim 5, wherein information for metering volume is located on an upper housing flange of the metering housing, said information interacting with a lug on the plunger.

*11. A dosing device for metered dispensing of a medium, comprising:*

*a metering housing for receiving a volume of the medium to be dispensed;*

*a plunger which is axially displaceable in the metering housing in a limited manner over a stroke of movement, the plunger having a plurality of channels of different lengths extending axially in a periphery of the plunger, and*

*a stroke limitation device comprising a projection associated with the metering housing which is configured to project into and interact with a selected one of the plurality of channels formed in the periphery of the plunger,*

*wherein the plunger is configured for rotation relative to the metering housing to select one of the plurality of channels, such that the projection projects into and interacts with the selected one of the channels to determine a length of the stroke of movement of the plunger and thereby also the volume of the medium to be dispensed, and to provide anti-twist protection.*

*12. The dosing device as claimed in claim 11, wherein the plunger is axially displaceable in the metering housing over the stroke of movement from a closed position, in which the plunger seals an intake opening at an end of the metering housing, such that during the movement of the plunger, the projection moves along the selected one of the channels until it abuts against an end of that channel.*

*13. The dosing device as claimed in claim 12, wherein the plunger seals the intake opening at the end of the metering housing in the closed position via a conical end journal.*

*14. The dosing device as claimed in claim 11, wherein the metering housing comprises an elongate, generally cylindrical tube having an intake opening at an end thereof for intake of the volume of the medium to be dispensed.*

*15. The dosing device as claimed in claim 11, wherein each of the plurality of channels has a channel inlet for receiving the projection.*

*16. The dosing device as claimed in claim 11, wherein the projection is provided on a stop ring mounted on the metering housing.*

*17. The dosing device as claimed in claim 16, wherein the stop ring forms a flange at an end region of the metering housing.*

*18. The dosing device as claimed in claim 11, wherein the projection projects into an axial recess of the metering housing within which the plunger is axially displaceable.*

*19. The dosing device as claimed in claim 18, wherein the plunger is supported against and seals against the axial recess of the metering housing via an annular lip.*

*20. The dosing device as claimed in claim 11, wherein markings that provide information concerning a metering amount are situated on a housing flange of the metering housing.*

* * * * *